United States Patent [19]

Bradshaw et al.

[11] 4,165,430
[45] Aug. 21, 1979

[54] CEPHALOSPORINS HAVING A 7-CARBOXY SUBSTITUTED α-ETHERIFIED OXIMINOARYLACETAMIDO) GROUP

[75] Inventors: Janice Bradshaw, Harrow; Martin C. Cook, Liverpool; Gordon I. Gregory, Chalfont St. Peter, all of England

[73] Assignee: Glaxo Laboratories Limited, Greenford, England

[21] Appl. No.: 696,276

[22] Filed: Jun. 15, 1976

Related U.S. Application Data

[63] Continuation-in-part of Ser. No. 668,529, Mar. 19, 1976, Pat. No. 4,103,084, which is a continuation of Ser. No. 533,451, Dec. 16, 1974, abandoned.

[51] Int. Cl.$^2$ .................. C07D 501/46; A61K 31/545
[52] U.S. Cl. ......................... 544/22; 544/16; 544/24; 544/25; 544/27; 424/246
[58] Field of Search ............... 260/243 C; 544/25, 24, 544/22, 16

[56] References Cited

U.S. PATENT DOCUMENTS 3,546,219 12/1970 Long et al. ...................... 260/243 C

FOREIGN PATENT DOCUMENTS

| | | |
|---|---|---|
| 806450 | 4/1974 | Belgium . |
| 2223375 | 1/1972 | Fed. Rep. of Germany . |
| 2204060 | 8/1972 | Fed. Rep. of Germany . |
| 2262500 | 7/1973 | Fed. Rep. of Germany . |
| 2460537 | 7/1975 | Fed. Rep. of Germany . |
| 68680 | 1/1974 | Luxembourg . |

Primary Examiner—Donald G. Daus
Assistant Examiner—Diana G. Rivers
Attorney, Agent, or Firm—Bacon & Thomas

[57] ABSTRACT

Cephalosporin antibiotics having the formula:

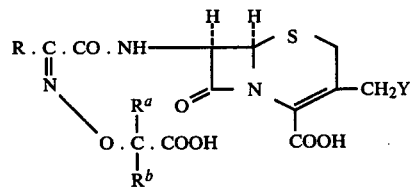

(where R is thienyl, furyl or phenyl; $R^a$ is hydrogen, $C_{1-4}$ alkyl, $C_{2-4}$ alkenyl, $C_{3-7}$ cycloalkyl or phenyl, and $R^b$ is hydrogen, $C_{1-4}$ alkyl, $C_{2-4}$ alkenyl, $C_{3-7}$ cycloalkyl, phenyl, carboxy or $C_{2-5}$ alkoxycarbonyl, or $R^a$ and $R^b$ together with the carbon atom to which they are attached form a $C_{3-7}$ cycloalkylidene or cycloalkenylidene group: and Y is the residue of a nitrogen nucleophile and their physiologically acceptable derivatives exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of *Escherichia coli, Haemophilus influenzae* and Proteus organisms; and unusually high activity against Pseudomonas organisms.

15 Claims, No Drawings

CEPHALOSPORINS HAVING A 7-CARBOXY SUBSTITUTED α-ETHERIFIED OXIMINOARYLACETAMIDO) GROUP

CROSS REFERENCE TO RELATED APPLICATIONS

This application is a continuation-in-part of our U.S. Application Ser. No. 668,529 filed Mar. 19, 1976, now U.S. Pat. No. 4,103,084, which is a continuation of our U.S. application Ser. No. 533,451 filed Dec. 16, 1974, now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Pseudomonas organisms are resistant to the majority of existing commerically available antibiotic compounds, and the practical therapeutic applications of aminoglycoside antibiotics such as gentamicin which do exhibit Pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides 7β-acylamidoceph-3-em-4-carboxylic acid antibiotics and non-toxic derivatives thereof. These antibiotics have the formula:

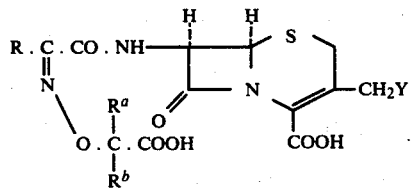

wherein
R is thienyl, furyl or phenyl;

$R^a$ is hydrogen, methyl, ethyl, propyl, isopropyl, butyl, allyl, cyclohexyl or phenyl;

$R^b$ is hydrogen, carboxy, $C_2$–$C_5$ alkoxycarbonyl, methyl, ethyl, propyl, isopropyl, butyl, allyl, cyclohexyl or phenyl;

or $R^a$ and $R^b$ together with the carbon atom to which they are attached form a $C_{3-7}$ cycloalkylidene group;

Y is the residue of a nitrogen nucleophile which is a tri($C_{1-6}$ alkyl) amine, or a heterocyclic tertiary amine which is a pyridine, pyrimidine, pyridazine, pyrazine, pyrazole, imidazole, triazole, thiazole, benzotriazole or purine, which may be substituted by a $C_{1-6}$ alkyl, phenyl, naphthyl, phenyl $C_{1-6}$ alkyl, ($C_{1-6}$ alkoxy) methyl, ($C_{2-7}$ alkanoyloxy)methyl, formyl, $C_{2-7}$ alkanoyl, $C_{2-7}$ alkanoyloxy, carboxy, $C_{2-7}$ alkoxycarbonyl, carboxy ($C_{1-6}$ alkyl), sulpho, $C_{1-6}$ alkoxy, phenoxy, phenyl $C_{1-6}$ alkoxy, $C_{1-6}$ alkylthio, phenylthio, phenyl $C_{1-6}$ alkylthio, cyano, hydroxy, carbamoyl, N-($C_{1-6}$ alkyl) carbamoyl, N,N-di($C_{1-6}$ alkyl) carbamoyl, N-(hydroxy $C_{1-6}$ alkyl)carbamoyl or carbamoyl $C_{1-6}$ alkyl group; or azido.

These compounds exist as syn isomers or exist as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae*, *Serratia marcescens* and *Klebsiella aerogenes*. The compounds have particularly high activity against strains of *Escherichia coli*, *Haemophilus influenzae* and Proteus organisms, e.g. strains of *Proteus morganii* and *Proteus mirabilis*. Compounds wherein at least one of $R^a$ and $R^b$ is other than hydrogen have also shown unusually high activity against Pseudomonas organisms, for example strains of *Pseudomonas aeruginosa*.

The compounds of the invention are defined as having the syn isomeric form as regards the configuration of the group

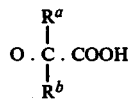

with respect to the carboxamido group. In this specification the syn configuration is denoted structurally as

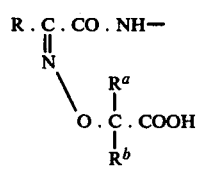

this configuration being assigned on the basis of the work of Ahmad and Spenser reported in *Can. J. Chem.*, 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The term "lower" as used in this specification and the accompanying claims to qualify aliphatic groups denotes, unless otherwise stated, that the said group may contain up to 6 carbon atoms. "Lower" as used to qualify cycloaliphatic groups indicates that the group may contain 3–7 (e.g. 5–7) carbon atoms.

A particularly interesting class of cephalosporin antibiotics in accordance with the invention comprises compounds of general formula

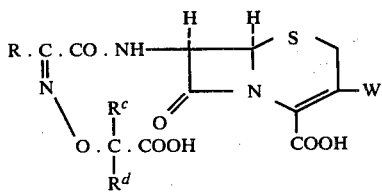

(II)

[wherein R is thienyl or furyl, $R^c$ represents methyl, ethyl, propyl, allyl or phenyl and $R^d$ represents hydrogen, carboxy or, more preferably, a group as defined for $R^c$; or $R^c$ and $R^d$ together with the carbon atom to which they are attached form a cyclobutylidene, cyclopentylidene or cyclohexylidene group; and W is selected from:

(i) the group $-CH_2G$ where G is the residue of a nitrogen nucleophile selected from compounds of the formula

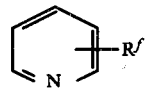

(wherein $R^f$ is hydrogen, carbamoyl, carboxymethyl or sulpho), and pyridazine; and (ii) azidomethyl and non-toxic derivatives thereof.

These compounds exhibit broad spectrum antibiotic activity (including very high activity against strains of *Haemophilus influenzae* and Proteus organisms) and high β-lactamase stability and are further characterised by particularly high in vitro activity against Pseudomonas organisms such as strains of *Pseudomonas aeruginosa*.

Especially preferred compounds of the above type, by virtue of their particularly high levels of activity against Proteus and Pseudomonas organisms, include the following:

(6R,7R)-7-[2-(2-carboxyprop-2-yloxyimino)-2-(fur-2-yl) acetamido]-3-pyridiniummethylceph-3-em-4-carboxylic acid (syn isomer), (6R,7R)-7-[2-(2-carboxyprop-2-yloxyimino)-2-(fur-2-yl) acetamido]-3-pyradiziniummethylceph-3-em-4-carboxylic acid (syn isomer), (6R,7R)-7-[2-(1-carboxycyclopent-1-yloxyimino)-2-(fur-2-yl) acetamido]-3-pyridiniummethylceph-3-em-4-carboxylic acid (syn isomer), and (6R,7R)-7-[2-(1-carboxycyclobut-1-yloxyimino)-2-(fur-2-yl)acetamido]-3-pyridiniummethylceph-3-em-4-carboxylic acid (syn isomer), and non-toxic derivatives thereof, e.g. alkali metal salts such as the sodium or potassium salts.

A further interesting class of cephalosporin antibiotics in accordance with the invention comprises compounds of general formula

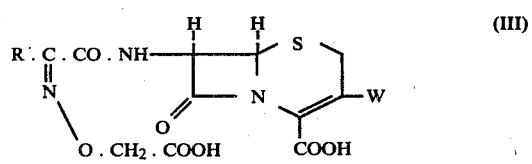

(III)

[wherein R is thienyl or furyl and W is as hereinbefore defined and non-toxic derivatives thereof.

These compounds exhibit broad spectrum antibiotic activity coupled with high β-lactamase stability. A characteristic feature of the compounds is their high activity against strains of *Haemophilus influenzae* coupled with their particularly high activity against strains of *Escherichia coli* and Proteus organisms.

A preferred compound of the above type, by virtue of its particularly high levels of activity against *Escherichia coli* and Proteus organisms, is:

(6R,7R)-3-azidomethyl-7-[2-carboxymethoxyimino-2-(fur-2-yl)acetamido]ceph-3-em-4-carboxylic acid (syn isomer), and non-toxic derivatives thereof, e.g. alkali metal salts such as the sodium or potassium salts.

The compounds according to the invention may be prepared by any convenient method, for example by techniques analagous to those described in Belgian Patent No. 783449.

Thus according to one embodiment of the invention we provide a process for the preparation of an antibiotic compound of general formula I as hereinbefore defined or a non-toxic derivative thereof which comprises either (A) condensing a compound of the formula

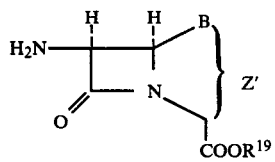

[wherein B is $>S$ or $>S \rightarrow O$ ($\alpha$- or $\beta$-); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1-20 carbon atoms) or a symmetrical or mixed anhydride group derived from an appropriate acid; and Z' is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

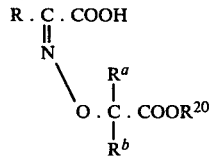

(wherein R, $R^a$ and $R^b$ are as hereinbefore defined and $R^{20}$ is a carboxyl blocking group, e.g. a group as hereinbefore defined in connection with $R^{19}$); or (B), reacting a compound of the formula

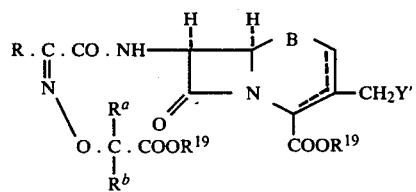

(wherein B,R,$R^a$ and $R^b$ are as hereinbefore defined; each $R^{19}$ may independently represent hydrogen or a carboxyl blocking group; Y' is a replaceable residue of a nucleophile, e.g. an acetoxy or dichloroacetoxy group or a halogen atom such as chlorine, bromine or iodine; and the dotted line bridging the 2-, 3- and 4-positions indicates that the compound is a ceph-2-em or ceph-3-em compound) with an appropriate nitrogen nucleophile; whereafter, if necessary and/or desired in each instance, any of the following reactions (C) in any appropriate sequence, are carried out:

(i) conversion of a $\Delta^2$ isomer into the desired $\Delta^3$ isomer,
(ii) reduction of a compound wherein B is $>S \rightarrow O$ to form a compound wherein B is $>S$,
(iii) removal of carboxyl blocking groups;

and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (V) or a salt thereof with a halogenating agent e.g. phosphorus pentachloride, thionyl chloride or oxalyl chloride. Treatment of the sodium, potassium or triethylammonium salt of the acid (V) with oxalyl chloride is advantageous in that under these conditions isomerisation is minimal.

Acylations employing acid halides may be effected in aqueous and non-aqueous reaction media, conveniently at temperatures of from $-50°$ to $+50°$ C., preferably $-20°$ to $+30°$ C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula V may themselves be used as acylating agents in the preparation of compounds of formula I. Acylations employing acids (V) are desirably conducted in the presence of a condensation agent, for example a carbodiimide such as N,N'-diethyl-, dipropyl- or diisopropylcarbodiimide, N,N'-dicyclohexylcarbodiimide or N-ethyl-N'-$\gamma$-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula V such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline.

Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Compounds of formula I may be prepared by the reaction of a 3-acetoxymethyl cephalosporin compound with a nitrogen nucleophile, as described in British Pat. Nos. 912,541; 1,012,943; 1,030,630; 1,082,943 and 1,082,962.

Compounds wherein Y is the residue of an appropriate nitrogen nucleophile may also be prepared by the reaction of a 3-halomethylcephalosporin with any of the nucleophiles disclosed in the above references, such a process being described in British Pat. No. 1,241,657, or by the reaction of a 3-halomethylcephalosporin sulphoxide with any of the nucleophiles disclosed in the above references, such a process being described in British Pat. No. 1,326,531. The contents of the above mentioned British Patents are herein incorporated for reference purposes.

Where a 3-halomethylcephalosporin sulphide or sulphoxide ester is reacted with a tertiary nitrogen nucleophile such as pyridine in accordance with the process of British Pat. Nos. 1,241,657 or 1,326,531, the reaction product will usually be obtained in the form of, for example, the corresponding 3-pyridiniummethyl halide. It has been observed that deesterification of compounds of this type by treatment with trifluoroacetic acid tends to promote isomerisation of the oxyimino moiety in the 7β-acylamido side chain; such isomerisation is clearly undesirable if a product containing at least 90% of the syn isomer is to be obtained without the need for a subsequent isomer separation stage.

It has also been observed, however, that the tendency to isomerisation may be substantially lessened if the 3-pyridiniummethyl halide is converted into the 3-pyridiniummethyl salt of a non-hydrohalic acid (e.g. trifluoroacetic, acetic, formic, sulphuric, nitric or phosphoric acid) prior to deesterification. Conversion of the halide salt into a non-hydrohalic acid salt is conveniently effected by means of anion exchange. This may be brought about by, for example, use of a suitable anion exchange resin, for example in the trifluoroacetate form. Where an anion exchange resin is employed, the 3-pyridiniummethyl halide may be run through a column of the resin prior to deesterification. Where the 3-pyridiniummethyl cephalosporin compound is a sulphide it may be advantageous to employ an inert organic solvent system (i.e., one which does not have a harmful effect on the resin) to ensure adequate solubility for the cephalosporin compound; organic solvent systems which may be used include lower alkanols such as ethanol, ketones such as acetone, and nitriles such as acetonitrile. Where the 3-pyridiniummethyl cephalosporin compound is a sulphoxide it may be preferable to employ an aqueous solvent system; the use of aqueous systems may promote simultaneous deesterification of the cephalosporin compound when, for example, an anion exchange resin in the trifluoroacetate form is employed.

Where Y is a halogen (i.e., chlorine, bromine or iodine) atom, ceph-3-em starting compounds may be prepared by halogenation of a 7β-acylamido-3-methyl-ceph-3-em-4-carboxylic acid ester 1β-oxide followed by reduction of the 1β-oxide group later in the sequence as described in British Pat. No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em compound.

Examples of appropriate nitrogen nucleophiles include tertiary aliphatic, aromatic, araliphatic and cyclic amines, for example tri($C_{1-6}$ alkyl) amines such as triethylamine, and heterocyclic tertiary amines. The heterocyclic tertiary amines may if desired contain one or more further heteroatoms in addition to the basic nitrogen atom, and may be substituted or unsubstituted. The heterocyclic tertiary amine may thus, for example, be a pyridine, pyrimidine, pyridazine, pyrazine, pyrazole, imidazole, triazole or thiazole; a fused bi- or poly-cyclic analogue of any of these heterocycles, for example purine or benzotriazole; and any of the above amines substituted by one or more aliphatic (e.g. lower alkyl such as methyl, ethyl, n-propyl or isopropyl), aryl (e.g. $C_{6-12}$ mono- or bicyclic carbocyclic aryl such as phenyl or naphthyl), araliphatic (e.g. phenyl lower alkyl such as benzyl or phenylethyl), lower alkoxymethyl (e.g. methoxymethyl, ethoxymethyl, n-propoxymethyl or iso-propoxymethyl), acyloxymethyl (e.g. lower alkanoyloxymethyl such as acetoxymethyl), formyl, acyloxy (e.g. lower alkanoyloxy such as acetoxy), carboxy, esterified carboxy (e.g. lower alkoxycarbonyl such as methoxycarbonyl), carboxy lower alkyl (e.g. carboxymethyl), sulpho, lower alkoxy (e.g. methoxy, ethoxy, n-propoxy or iso-propoxy), aryloxy (e.g. phenoxy), aralkoxy (e.g. benzyloxy), alkylthio (e.g. methylthio or ethylthio), arylthio, aralkylthio, cyano, hydroxy, carbamoyl, N-monoloweralkylcarbamoyl (e.g. N-methylcarbamoyl or N-ethylcarbamoyl), N,N-diloweralkylcarbamoyl (e.g. N,N-dimethylcarbamoyl or N,N-diethylcarbamoyl), N-(hydroxyloweralkyl)carbamoyl (e.g. N-(hydroxymethyl)carbamoyl or N-(hydroxyethyl)-carbamoyl), or carbamoylloweralkyl (e.g. carbamoylmethyl or carbamoylethyl) groups. Examples of Y groups which may be obtained from heterocyclic tertiary amine nucleophiles of the above type include pyridinium, 3- and 4-carbamoylpyridinium, 3-carboxymethylpyridinium, 3-sulphopyridinium, thiazol-3-yl, pyrazol-1-yl, pyridazininium, and benzotriazol-1-yl.

Another class of nitrogen nucleophiles comprises azides, e.g. alkali metal azides such as sodium azide.

Δ²-Cephalosporin ester derivatives obtained in accordance with the process of the invention may be converted into the corresponding Δ³ derivative by, for example, treatment of the Δ² ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is >S→O this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-$d_6$ solutions of syn compounds of Formula I exhibit the doublet for the amide NH at a lower field than do similar solutions of the corresponding anti-isomers. These factors may be employed in monitoring reactions.

Acids (V) may be obtained by reacting a glyoxylic acid of formula

R.CO.COOH  (VII)

(where R has the above-defined meaning) or an ester thereof with a hydroxylamine derivative of formula

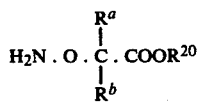 (VIII)

$$H_2N.O.C(R^a)(R^b).COOR^{20}$$

(where $R^a$, $R^b$, and $R^{20}$ have the above-defined meanings). The resulting acid or ester may be separated into its syn and anti isomers by, for example, crystallisation, chromatography or distillation, whereafter ester derivatives may be hydrolysed to yield the corresponding acid.

Acids (V) may also be prepared by etherification of an acid of formula

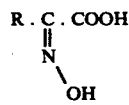 (IX)

(where R has the above-defined meaning), e.g. by reaction with a compound of general formula

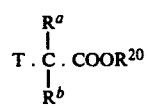 (X)

$$T.C(R^a)(R^b).COOR^{20}$$

(wherein $R^a$, $R^b$, and $R^{20}$ are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction.

Acids of formula V and acylating agents derived therefrom (e.g. acyl halides such as the chloride) are novel and comprise a feature of the present invention.

Derivatives of the compounds of the invention in which the carboxy substituent of the 7β-acylamido side chain is substituted by a carboxyl blocking group are also new and comprise a feature of the invention. These monoester derivatives, which may be represented by the general formula

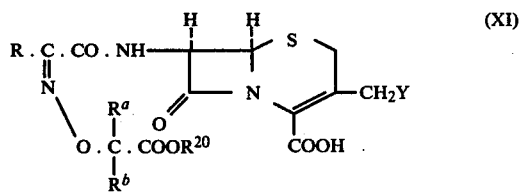 (XI)

(wherein R, $R^a$, $R^b$ and Y are as hereinbefore defined and $R^{20}$ is a carboxyl blocking group such as t-butyl or diphenylmethyl), are of value as intermediates in the preparation of antibiotic compounds of general formula I. The compounds (XI) may themselves exhibit antibiotic activity, although generally at a very low level when compared to corresponding compounds (I).

Carboxyl blocking groups $R^{20}$ and, where appropriate, $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for verterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in °C. The structure of the products were verified by p.m.r. spectroscopy (Preparations and Examples) and i.r. spectroscopy (Examples only).

PREPARATION 1

2-t-Butoxycarbonylmethoxyimino-2-(fur-2-yl)acetic acid (syn isomer)

The pH of a mixture of fur-2-ylglyoxylic acid (4.2 g), t-butoxycarbonylmethoxyamine (4.5 g) and water (50 ml) was adjusted to 5.0 with 2 N sodium hydroxide solution. The resulting solution was stirred for 16 hours. The pH of the solution was increased to 7.0, and the solution was washed twice with ether. The aqueous solution was acidified to pH 1.8 under ether, and further extracted with ether. The combined ether extracts were washed (water, saturated brine), dried, and concentrated to give a solid (7.62 g), which was crystallised from carbon tetrachloride to give the title compound (3.67 g, 46%) m.p. 105.1°–106.2°; $\lambda_{max}$ (pH 6 phosphate buffer) 277.5 nm ($\epsilon$ 16,300).

PREPARATION 2

2-(2-t-Butoxycarbonylprop-2-yloxyimino)-2-(fur-2-yl)acetic acid (syn isomer)

A solution of 2-(fur-2-yl)-2-hydroxyiminoacetic acid (syn isomer) (14.1 g) in dimethyl sulphoxide (100 ml) was added all at once to a magnetically stirred solution of potassium t-butoxide (22.4 g) in dimethyl sulphoxide (400 ml), the reaction mixture being maintained under an atmosphere of dry nitrogen. A gel was formed which, on stirring, become a finely divided, yellow solid. Stirring was continued for one hour, and then a solution of t-butyl 2-bromo-2-methylpropionate (24.0 g) in dimethyl sulphoxide (50 ml) was added over one hour to the reaction mixture at room temperature. After addition was complete, the resulting solution was stirred for a further hour. The reaction was poured into ice-water (1.5 liters) and acidified under ether (500 ml) to pH 1.8 with concentrated hydrochloric acid. The two layers were separated, and the aqueous layer was extracted with more ether. The combined ether extracts were washed once with water, then extracted with aqueous sodium bicarbonate solution. The combined alkaline extracts were acidified under ether to pH 1.8 with concentrated hydrochloric acid, and the acid solution was extracted further with ether. The combined ether extracts were washed (water, saturated brine), dried, and concentrated to a yellow oil, which crystallised under high vacuum (22.41 g, 83%), $\lambda_{max}$ (EtOH) 272.5 nm ($\epsilon$ 15,400).

The above solid (22.4 g) was crystallised from carbon tetrachloride (25 ml) to give the title compound (16.42 g, 61%), m.p. 72.5°–74.2° (73.0°).

PREPARATIONS 3 AND 4

Method A

The dipotassium salt of 2-(fur-2-yl)-2-hydroxyiminoacetic acid (syn isomer) was generated under an atmosphere of dry nitrogen and alkylated with the appropriate halo-t-butyl ester as described in Preparation 2. The products were isolated by pouring into water, acidifying, and extracting in the conventional manner.

TABLE 1

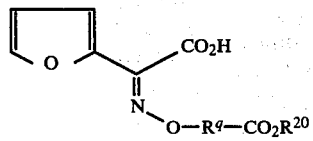

| Preparation No. | R$^q$ | R$^{20}$ | Method | m.p. °C. | λ$_{max}$, nm (solvent) | ε |
|---|---|---|---|---|---|---|
| 3 | (cyclopentyl) | —C(CH$_3$)$_3$ | A | 106.8°–107.3° | 277.5(pH6 buffer) | 15,100 |
| 4 | (cyclobutyl-like) | —C(CH$_3$)$_3$ | A | 113°–114° | 278(pH6 buffer) | 17,200 |

| Preparation No. | τ values for d$_6$-DMSO | |
|---|---|---|
|  | R$^q$ | R$^{20}$ |
| 3 | 8.03; 8.30 | 8.63 |
| 4 | 7.4–8.3 | 8.59 |

PREPARATION 5 syn-2-(2-tert-Butoxycarbonylprop-2-yloxyimino)-phenylacetic acid

To a well-stirred solution of potassium tert-butoxide (449 mg, 4 mmole) in dry DMSO (10 ml) was added in one portion a solution of syn-2-hydroxyiminophenylacetic acid (330 mg, 2 mmole) in DMSO (5 ml). The mixture was stirred for 45 minutes, then tert-butyl α-bromoisobutyrate (446 mg, 2 mmole) in DMSO (5 ml) was added. The mixture was stirred for 3.5 hr at room temperature, then poured into ice-water (150 ml). Ether (125 ml) was added and the pH was adjusted to 1.5 (conc. HCl). The aqueous layer was again extracted with ether, and the ether extracts washed with water and extracted into saturated sodium bicarbonate solution. The extract was acidified (pH 1.5) and extracted with ether. The ether layer was separated and washed with water and dried (Na$_2$SO$_4$). Evaporation left an oil, which later solidified. The product was dissolved in methylene chloride (8 ml) and filtered, and the filtrate was evaporated, leaving an off-white solid (310 mg, 50%), m.p. 102°–105°, λ$_{max}$ (EtOH) 253.5 nm (ε 12,700).

PREPARATION 6

Syn-tert-Butoxycarbonylmethoxyiminophenylacetic acid

A mixture of phenyl glyoxylic acid and an excess (10 to 15%) of t-butoxycarbonylmethoxyamine hydrochloride was suspended in aqueous ethanol, stirred, and the pH of the mixture adjusted to between 4 and 5 with sodium hydroxide solution (N to 10 N). A clear solution at pH 4 to 5 was maintained during the reaction by further additions of sodium hydroxide solution and ethanol as needed. The reaction mixture was kept at room temperature until all of the keto-acid was consumed. The progress of the reaction was followed by acidification of an aliquot, extraction with ethyl acetate and thin layer chromatography of the extract on silica plates (developed with a mixture of chloroform: methanol: acetic acid; 18:2:1). The t-butoxycarbonylmethoxyiminoacetic acid was less polar than the starting keto-acid. When reaction was complete the pH of the mixture was adjusted to between 7 and 8 and the ethanol (if any) was removed by evaporation. The aqueous mixture was extracted with ether, the extract discarded and the aqueous phase acidified to pH <2 with dilute hydrochloric acid. The mixture was extracted with ethyl acetate, the extract dried and evaporated to give the crude product which was purified by crystallisation and recrystallisation from carbon tetrachloride. M.pt. 88.5°, λ$_{max}$ (EtOH) 253 nm (ε 13,800).

EXAMPLE 1

(a)

(6R,7R)-3-Acetoxymethyl-7-[2-t-butoxycarbonylmethoxyimino-2-(fur-2-yl)acetamido]ceph-3-em-4-carboxylic acid (syn isomer)

Oxalyl chloride (0.45 ml) was added at 5° to a stirred solution of 2-t-butoxycarbonylmethoxyimino-2-(fur-2-yl)acetic acid (syn isomer) (1.35 g) in dry dichloromethane (50 ml) containing triethylamine (0.7 ml) and dimethylformamide (1 drop). The solution was stirred at 5° for one hour and was then evaporated to dryness at 5°. The residue was suspended in acetone (50 ml) and was added over 30 minutes to a stirred, ice-cooled solution of (6R,7R)-3-acetoxymethyl-7-aminoceph-3-em-4-carboxylic acid (1.36 g) in water (100 ml) and acetone (50 ml) containing sodium bicarbonate (1.0 g). The reaction mixture was stirred for one hour, whereafter the acetone was evaporated under reduced pressure. The residue was acidified to pH 1.8, and this mixture was extracted with ether. The combined extracts were washed (water, saturated brine), dried, and evaporated to give the title compound (2.52 g, 96%) as a pale yellow foam, [α]$_D$+28.5° (c 0.96, DMSO); λ$_{max}$ (pH 6 phosphate buffer) 276.5 nm (ε 17,900).

(b)

(6R,7R)-3-Acetoxymethyl-7-[2-carboxymethoxyimino-2-(fur-2-yl)-acetamido]ceph-3-em-4-carboxylic acid, disodium salt (syn isomer)

A solution of (6R,7R)-3-acetoxymethyl-7-[2-t-butoxycarbonylmethoxyimino-2-(fur-2-yl)acetamido]ceph-3- em-4-carboxylic acid (syn isomer) (1.422 g) and anisole (0.25 ml) in trifluoroacetic acid (5 ml) was kept at ambient temperature for 5 minutes. The mixture was concentrated at reduced pressure, ethyl acetate (10 ml) was added, and the mixture was re-evaporated. The residue was distributed between ether and sodium bicarbonate solution. The ether layer was extracted further with sodium bicarbonate solution and the combined alkaline extracts were acidified to pH 1.8 under ether. The acid mixture was extracted with ether, and the combined ether extracts were washed (water, saturated brine), dried, and evaporated to give the dicarboxylic acid corresponding to the title compound (942 mg, 74%), τ (d$_6$ - DMSO) values include 0.24 (d, J 8 Hz, N$\underline{H}$), 4.13 (dd, 7-$\underline{H}$), and 5.31 (s, C$\underline{H}_2$CO$_2$H).

This di-acid (900 mg) in acetone (9 ml) was neutralised with a solution of sodium 2-ethylhexanoate (700 mg) in acetone (5 ml). The mixture was stirred for 10 minutes, then the precipitated solid was filtered off, washed with a little acetone, and dried to give the title compound (807 mg, 60%), [α]$_D$+15° (c 1.08, DMSO); λ$_{max}$ (Nujol) 1766 cm$^{-1}$ (β-lactam).

EXAMPLES 2–5

General Procedure for the Preparation of (6R,7R)-7-(2-Aryl-2-carboxy-R$^q$-oxyiminoacetamido)-3-(substituted) ceph-3-em-4-carboxylic Acids (syn-isomers) and/or their Salts

Method A

Following the procedure described in Example 1, a solution of the appropriate 2-aryl-2-t-butoxycarbonyl-R$^q$-oxyiminoacetic acid (syn-isomer) (1 equiv) in methylene chloride optionally containing a few drops of N,N-dimethylformamide and triethylamine (1 equiv) was treated with oxalyl chloride (1 equiv) at 0°–5° for ca. 1 hour. The mixture was then evaporated to dryness. The residue was suspended or dissolved in acetone and added to a stirred, ice-cold solution of (6R,7R)-3-acetoxymethyl-7-aminoceph-3-em-4-carboxylic acid (1–1.2 equiv) in water or a mixture of acetone and water containing sodium hydrogen carbonate (2–2.5 equiv). The reaction mixture was stirred for 0.5–2.5 hours, allowing the temperature to rise to room temperature, whereafter the acetone was removed under reduced pressure. The pH was adjusted to 1.5–2.0 and the product extracted into ethyl acetate (alternatively ether or methylene chloride may be used). The organic layer was washed with water and/or saturated brine, dried and evaporated to give the corresponding (6R,7R)-3-acetoxymethyl-7-(2-aryl-2-t-butoxycarbonyl-R$^q$-oxyiminoacetamido)ceph-3-em-4-carboxylic acid (syn-isomer) which was characterised by optical rotation and/or by spectroscopy.

The t-butyl esters were deprotected by treating with trifluoracetic acid containing anisole at room temperature for at least 5 minutes. The reaction mixture was evaporated in vacuo and the product isolated by trituration or by distributing between ethyl acetate (or ether) and an aqueous solution of sodium hydrogen carbonate, separating the aqueous extracts, acidifying these extracts under ethyl acetate and isolating the title dicarboxylic acid in the usual way. The products are listed in Table 2.

Method B

As Method A except that the dicarboxylic acid was converted into its disodium salt by treating a solution of the acid in acetone with a solution of sodium 2-ethylhexanoate in acetone. The precipitated disodium salt was washed and dried. The products are listed in Table 2.

Method C

As Method A except that a (6R,7R)-3(substituted methyl)-7-aminoceph-3-em-4-carboxylic acid or salt thereof was used in place of (6R,7R)-3-acetoxymethyl-7-aminoceph-3-em-4-carboxylic acid. The products are listed in Table 3.

TABLE 2

| Ex. No. | R$^p$ | R$^q$ | Salt | Method | [α]$_D$ (DMSO) | λ$_{max}$,nm (pH 6 buffer) | ε | β-lactam ν$_{max}$, cm$^{-1}$ (Nujol) |
|---|---|---|---|---|---|---|---|---|
| 2 | furyl | >C(CH$_3$)$_2$ | disodium | A,B | +95° | 274 | 16,800 | 1768 |
| 3 | furyl | cyclopentyl | disodium | A,B | +62° | 276 | 16,800 | 1756 |
| 4 | furyl | cyclobutyl-methyl | — | A, | +28° | 274 | 14,600 | 1780 |

| Ex. No. | τ values* for d$_6$-DMSO at 100 MHz | | |
|---|---|---|---|
| | x | y | R$^q$ |

TABLE 2-continued

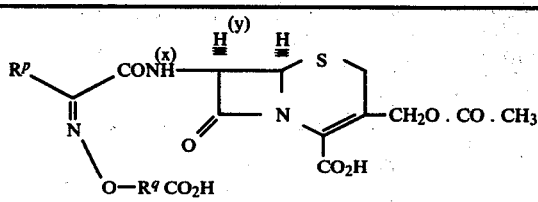

| | | | |
|---|---|---|---|
| 2. | 0.32 | 4.05 | 8.47 |
| 3. | 0.38 | 4.10 | 7.90 and 8.28 |
| 4. | 0.31 | 4.09 | 7.56, 8.08 |

*Values for free acids

TABLE 3

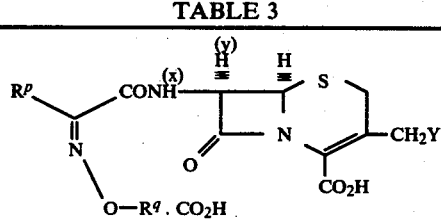

| Ex. No. | $R^p$ | $R^q$ | Y | Salt | Method | $[\alpha]_D$ (solvent) | $\lambda_{max}$, nm (pH6 buffer) | $\epsilon$ | $\beta$-lactam $\nu_{max}$, cm$^{-1}$ (Nujol) |
|---|---|---|---|---|---|---|---|---|---|
| 5 | (furyl) | —CH$_2$— | —N$_3$ | — | C | +35° (dioxan) | 275 | 15,200 | 1770 |

| Ex. No. | $\tau^*$ values for d$_6$-DMSO at 100 MHz | | |
|---|---|---|---|
| | x | y | $R^q$ |
| 5. | 0.14 | 4.10 | 5.31 |

EXAMPLE 6

Potassium (6R,7R)-7-[2-carboxymethoxyimino-2-(fur-2-yl) acetamido]-3-pyridiniummethyl-ceph-3-em-4-carboxylate (syn isomer)

A mixture of (6R,7R)-3-acetoxymethyl-7-[2-carboxymethoxyimino-2-(fur-2-yl)acetamido]ceph-3-em-4-carboxylate (syn isomer) (3.26 g), potassium thiocyanate (5.25 g), pyridine (0.72 ml) and water (2 ml) was stirred and heated for 40 minutes at 80°. The cooled reaction mixture was diluted with water (5 ml) and adsorbed on a column of XAD-2 resin (500 g). Components of the reaction mixture were eluted, first with water and then with aqueous ethanol (1:3) and collected using an automatic fraction collector. Those fractions having the characteristic ultraviolet absorption pattern of the required product were combined and evaporated to dryness in vacuo at <35°. The crude material (600 mg) was crystallised from aqueous acetone (1:9) to give the title compound (295 mg); $\lambda_{max}$ (pH 6 phosphate buffer) 261 nm ($\epsilon$ 19,000); $\lambda_{infl}$ 275 nm ($\epsilon$ 18,400).

EXAMPLE 7

Potassium (6R,7R)-7-[2-carboxyprop-2-yloxyimino-2-(fur-2-yl)-acetamido]-3-pyridiniummethyl-ceph-3-em-4-carboxylate (syn isomer)

A mixture of (6R,7R)-3-acetoxymethyl-7-[2-(carboxyprop-2-yloxyimino)-2-(fur-2-yl)acetamido]ceph-3-em-4-carboxylic acid (syn isomer) (4.0 g), pyridine (4 ml) and water (40 ml) was heated for 1 hour at 80°, whereafter the mixture was allowed to cool. The cooled mixture was diluted with water (50 ml) and extracted five times with methylene chloride (25 ml) and the combined organic extracts were washed with water. The combined aqueous phases were evaporated in vacuo at <35° to ca 50 ml and acidified to pH 2 with 2N-hydrochloric acid. The precipitated solid was removed by filtration, the filtrate was adjusted to pH 6.5 with potassium bicarbonate and the solution was concentrated in vacuo at <35° to ca. 40 ml. The product was purified on a column of XAD-2 resin (500 g), elution being effected with water and then aqueous ethanol (1:3). Fractions having the characteristic ultraviolet absorption of the product were combined and evaporated to dryness in vacuo at <35° to give the title compound (880 mg), $\lambda_{max}$ (H$_2$O) 261 and 277 nm ($\epsilon$17,000 and 16,950).

EXAMPLE 8

Sodium (6R,7R)-7-[2-(carboxyprop-2-yloxyimino)-2-(fur-2-yl)-acetamido]-3-pyridiniummethylceph-3-em-4-carboxylate (syn isomer)

A mixture of sodium iodide (50.0 g), water (15.5 ml) and pyridine (14 ml) was heated to 80° and stirred vigorously during the addition over a period of ca 10 minutes of (6R,7R)-3-acetoxymethyl-7-[2-(carboxyprop-2-yloxyimino)-2-(fur-2-yl)acetamido]ceph-3-em-4-carboxylate (syn isomer) (14.4 g). The mixture was stirred at 80° for a total of 55 minutes and was then cooled and diluted to ca 400 ml with water. 0.1 N-Sodium hydroxide was added to adjust the pH to ca 6.5 and the solution was concentrated under reduced pressure at <40° to a volume of ca 100 ml. The resulting solution was diluted to ca 400 ml with water, methyl isobutyl ketone (0.3 ml) was added and the stirred solution was acidified with 2N-hydrochloric acid (15 ml) to achieve a pH of 1-2. The solid was collected, washed with water and discarded. The filtrate and washings were treated with more 2N-hydrochloric acid (ca 10 ml) and extracted with ethyl acetate, the organic layer being re-extracted with a small volume of water. The aqueous phase was adjusted to pH 6 with 1N-sodium hydroxide (ca 43 ml) and evaporated under reduced pressure at <40° to a volume of ca 175 ml. This solution was applied to a column of XAD-2 resin (700 g, 42 cm×5.5 cm) that had previously been washed with water (2 liters). The column was eluted with water, the fractions being collected automatically and monitored by U.V. spectroscopy. When the inorganic salts and some impurities had been removed the eluant was changed to a mixture of ethanol and water (1:4). The fractions having the characteristic U.V. absorption of the product were combined, concentrated under reduced pressure at <40° then freeze-dried. The product was dried over phosphorus pentoxide in vacuo giving the title salt (4.10 g); $[\alpha]_D + 10.5°$ (c 1.00, $H_2O$); $\lambda_{max}$ (pH 6 buffer) 261.5 and 278.5 nm ($\epsilon$ 20,100; 19,200); $\nu_{max}$ (Nujol) 1770 cm$^{-1}$ ($\beta$-lactam); $\tau$ ($D_2O$, 100 MHz) values include 1.03, 1.43, 1.91 (pyridinium protons), 4.12 (dd, 7-$\underline{H}$) and 8.50 (s, C(C$\underline{H}_3$)$_2$).

EXAMPLES 9-14

In the manner of Example 8 the acetoxy group of (6R,7R)-3-acetoxymethyl-7-[2-(carboxy-R$^q$-oxyimino)-2-(fur-2-yl)acetamido]ceph-3-em-4-carboxylic acid (syn isomers) were displaced by treatment with pyridine or a substituted pyridine in aqueous sodium iodide solution at 80° for 45-60 minutes. The products were purified as the sodium salts by XAD-2 chromatography and their physical properties are summarised in Table 4.

TABLE 4

| Ex. No. | R$^q$ | P | Salt | $[\alpha]_D$ | $\lambda_{max}$, nm (pH 6 buffer) | $\epsilon$ | $\beta$-lactam $\nu_{max}$, cm$^{-1}$ (Nujol) |
|---|---|---|---|---|---|---|---|
| 9 | —CH$_2$— | CH$_2$—N$^+$⟨pyridine⟩ | monosodium | — | 260.5 278 | 14,500 14,100 | |
| 10 | >C(CH$_3$)$_2$ | CH$_2$N$^+$⟨pyridine⟩CONH$_2$ | monosodium | — | — | — | |
| 11 | >C(CH$_3$)$_2$ | CH$_2$N$^+$⟨pyridine⟩CH$_2$CO$_2$Na | disodium | — | 270.5 | 19,100 | |
| 12 | (cyclopentyl) | CH$_2$N$^+$⟨pyridine⟩ | monosodium | — | 260.5 280.5 | 19,100 19,100 | — |

| Ex. No. | $\tau$ values for $D_2O$ at 100 MHz | | |
|---|---|---|---|
| | x | y | R$^q$ |
| 9 | — | 4.16 | 5.45 |
| 10 | — | 4.11 | 8.48 |
| 11 | — | 4.11 | 8.48 |
| 12 | — | 4.16 | 7.92; 8.30 |

| Ex. No. | R$^q$ | P | Salt | $[\alpha]_D$ | $\lambda_{max}$, nm (pH 6 buffer) | $\epsilon$ | $\beta$-lactam $\nu_{max}$, cm$^{-1}$ (Nujol) |
|---|---|---|---|---|---|---|---|
| 13 | (cyclobutyl) | CH$_2$N$^+$⟨pyridine⟩ | monosodium | +14° ($H_2O$) | 260 280.5 | 19,400 18,550 | 1770 |

TABLE 4-continued

[Structure: furan-CH=N-O-R^q-CO2H group linked via C(=N-O...)-CONH-(x)H to β-lactam ring with H(y), S, fused to N-containing ring with CO2H and CH2-P substituent]

| Ex. No. | | | | |
|---|---|---|---|---|
| 14 | >C(CH₃)₂ | CH₂N⁺—(pyridinium) | — | 258 (EtOH) | 18,300 | 1770 |

| Ex. No. | $\tau$ values for D₂O at 100 MHz | | |
|---|---|---|---|
| | x | y | R$^q$ |
| 13 | — | 4.11 | 7.58; 8.03 |
| 14 | — | 4.22 | 8.50; 8.59 |

EXAMPLE 15

(6R,7R)-7-[2-(2-Carboxyprop-2-yloxyimino)-2-(fur-2-yl)-acetamido]-3-pyridaziniummethylceph-3-em-4-carboxylic acid trifluoroacetate (syn isomer)

(a) A suspension of diphenylmethyl (1S,6R,7R)-3-bromomethyl-7-[2-(2-t-butoxycarbonylprop-2-yloxyimino)-2-(fur-2-yl)acetamido]ceph-3-em-4-carboxylate 1-oxide (syn isomer) (1.51 g) in N,N-dimethylformamide (1 ml) was treated with pyridazine (400 mg). The mixture was stirred for 2 hours at 25° to give a clear solution, which was then diluted with ether (50 ml, added slowly with stirring). The resulting precipitate was filtered off, washed with ether and dried to give diphenylmethyl (1S,6R,7R)-7-[2-(2-t-butoxycarbonylprop-2-yloxyimino)-2-(fur-2-yl)acetamido]-3-pyridaziniummethylceph-3-em-4-carboxylate 1-oxide bromide (syn isomer) as a pink powder (1.59 g, 94%); [α]$_D$+13° (c 1.07, DMSO); λ$_{max}$ (EtOH) 277 nm (ε 21,200); ν$_{max}$ (Nujol) 1790 cm$^{-1}$ (β-lactam); τ (d$_6$-DMSO) values include 1.21 (d, J 8Hz, NH), 3.76 (dd, J 4 and 8Hz, 7-H), 8.51 (s, C(CH₃)₂) and 8.61 (s, C(CH₃)₃).

(b) The product of (a) above (1.49 g) in N,N-dimethylformamide (5 ml) at −10° was treated with potassium iodide (1.33 g) and then with acetyl chloride (0.28 ml). The mixture was stirred for 1 hour while the temperature slowly rose to 0°, and was then added dropwise to a stirred solution of sodium metabisulphite (1 g) in water (50 ml). The resulting suspension was stirred for 10 minutes and then the solid material was filtered off, washed with water and dried over phosphorus pentoxide to give a light brown powder (1.28 g). This material, in acetone:ethanol=9:1 (20 ml), was passed down a column of Deacidite FF resin (trifluoroacetate form, 15 cm×2.5 cm i.d.) which was eluted with the same solvent mixture. Eluant fractions containing ultraviolet light absorbing material were combined and evaporated, and the residue was triturated with ether to give diphenylmethyl (6R,7R)-7-[2-(2-t-butoxycarbonylprop-2-yloxyimino)-2-(fur-2-yl)acetamido]-3-pyridaziniummethylceph-3-em-4-carboxylate trifluoroacetate (syn isomer), (1.24 g, 82%); [α]$_D$−20° (c 0.76, DMSO); λ$_{max}$ (EtOH) 278 nm (ε 18,300); ν$_{max}$ (Nujol) 1780 cm$^{-1}$; τ (d$_6$-DMSO) values include 0.30 (d, J8Hz, NH), 3.95 (dd, J 5 and 8 Hz, 7-H), 8.55 (s, C(CH₃)₂) and 8.59 (s, C(CH₃)₃).

(c) The product of (b) above (1.13 g), mixed with anisole (1.5 ml), was treated with trifluoroacetic acid (6 ml) at 5° for 5 minutes, and then at 20° for 55 minutes. The solution was evaporated in vacuo, the residue was stirred with ethyl acetate, and the evaporation repeated. The resulting gum was triturated with ether to give the crude product as a pale brown solid, which was filtered off, washed with ether and dried. This was extracted with water (3 × 150 ml); the extracts were filtered, washed with ethyl acetate and then ether, and finally freeze-dried. The combined residues were triturated with ether to give the title salt as a white powder (586 mg, 72%); [α]$_D$+48° (c 0.98, DMSO); λ$_{max}$ (pH 6 phosphate buffer) 277 nm (ε 18,100); ξ$_{max}$ (Nujol) 1776 cm$^{-1}$ (β-lactam); τ (d$_6$-DMSO) 0.37 (d J 8 Hz, NH), 4.09 (dd, J 5 and 8 Hz, 7-H) and 8.53 (s, C(CH₃)₂).

EXAMPLES 16–20

The trifluoroacetate salts listed in Table 5 were prepared by reacting the 3-bromomethyl ester (see below) with the appropriate tertiary base, reducing the sulphoxide and removing both protecting groups in a similar manner to that described in Example 15 The starting material was prepared as follows:

A solution of phosphorus pentachloride (5.20 g) in dry dichloromethane (60 ml) at −10° was treated with N,N-dimethylacetamide (12 ml), and then with 2-(2-t-butoxycarbonylprop-2-yloxyimino)-2-(fur-2-yl)acetic acid (syn isomer) (6.43 g) added portionwise. The solution was stirred at −10° for 15 minutes and then ice (14 g) was slowly added and the temperature allowed to rise to 0° over 10 minutes. The organic layer was separated and added dropwise to a suspension of diphenylmethyl (1S,6R,7R)-7-amino-3-bromomethylceph-3-em-4-carboxylate 1-oxide hydrobromide (10.62 g) in dichloromethane (80 ml) containing propylene oxide (15 ml) at 0°. The mixture was stirred for 1 hour during which time the temperature rose to 20° and the suspension cleared. The resulting yellow solution was washed with 2.5% aqueous sodium bicarbonate solution (50 ml) and then 2N-hydrochloric acid (50 ml), whereafter the solution was dried and evaporated to a yellow oil. This material, in ethyl acetate (20 ml), was added dropwise to stirred petrol (b.p. 40°–60°) to give a gummy precipitate. The supernatant was decanted off and the gum chromatographed on a column of Kieselgel, which was eluted with dichloromethane containing from 0 to 10% acetone. Eluant fractions containing the main product were combined and evaporated to a foam. Trituration with cyclohexane gave diphenylmethyl (1S,6R,7R)-3-bromomethyl-7-[2-(2-t-butoxycarbonylprop-2-yloxyimino)-2-(fur-2-yl)-acetamido]ceph-3-em-4-carboxylate 1-oxide (syn isomer) as a pale yellow microcrystalline powder (13.61 g, 90%); $[\alpha]_D$ −22° (c 1.0, DMSO); $\lambda_{max}$ (EtOH) 281 nm ($\epsilon$ 22,200); $\nu_{max}$ (CHBr$_3$) 1800 cm$^{-1}$ ($\beta$-lactam); $\tau$ (d$_6$ DMSO) values include 1.26 (d, J 8 Hz, NH), 3.86 (dd, J 4 and 8 Hz, 7-H), 8.51 (s, C(CH$_3$)$_2$) and 8.61 (s, C(CH$_3$)$_3$).

washed twice with 2N-hydrochloric acid; the solution was then dried and evaporated, and the main product was isolated from the residue by column chromatography on Kieselgel, with chloroform containing 0 to 10% v/v acetone for elution. This material (700 mg) in N,N-dimethylformamide (2 ml) with potassium iodide (665 mg) at −10° was treated with acetyl chloride (0.14 ml). The suspension was stirred for 1.25 hours and allowed to warm slowly to 0°, and was then added dropwise to water (40 ml) containing sodium metabisulphite (0.5 g). The precipitate was filtered off, washed with water,

TABLE 5

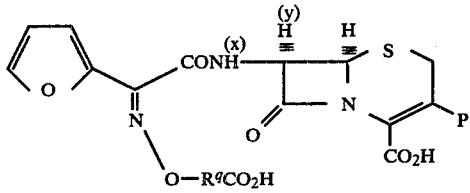

| Ex. No. | $R^q$ | P | Salt | $[\alpha]_D$ (DMSO) | $\lambda_{max}$, nm (pH 6 buffer) | $\epsilon$ | $\beta$-lactam $\nu_{max}$, cm$^{-1}$ (Nujol) |
|---|---|---|---|---|---|---|---|
| 16 | >C(CH$_3$)$_2$ | CH$_2$N$^+$–⟨⟩–CONH$_2$ | trifluoroacetate | −57.5° | 267 | 21,600 | 1775 |
| 17 | >C(CH$_3$)$_2$ | CH$_2$N$^+$–⟨S⟩ | trifluoroacetate | −43.5° | 244 277 | 14,800 18,200 | 1784 |
| 18 | >C(CH$_3$)$_2$ | CH$_2$N$^+$–⟨⟩–SO$_3$H | trifluoracetate | −58° | 267 | 22,200 | 1780 |
| 19 | C(CH$_3$)$_2$ | CH$_2$N$^+$–⟨N⟩–CH$_3$ | trifluoroacetate | −79° | 225.5 271 | 16,100 18,400 | 1778 |
| 20 | C(CH$_3$)$_2$ | CH$_2$N$^+$–⟨⟩N—CH$_3$ | trifluoroacetate | −32° | 274 | 18,100 | 1713 |

| Ex. No. | $\tau$ values* for d$_6$-DMSO at 100 MHz | | |
|---|---|---|---|
| | x | y | $R^q$ |
| 16 | 0.38 | 4.11 | 8.55 |
| 17 | 0.4 | 4.14 | 8.54 |
| 18 | 0.29 | 4.05 | 8.55 |
| 19 | 0.38 | 4.12 | 8.50 |
| 20 | 0.40 | 4.11 | 8.53 |

*Values for the trifluoroacetate salt

EXAMPLE 21

(6R,7R)-3-(Benzotriazol-1-ylmethyl)-7-[2-(2-carboxyprop-2-yloxyimino)-2-(fur-2-yl)acetamido]ceph-3-em-4-carboxylic acid (syn isomer)

Diphenylmethyl (1S,6R,7R)-3-bromomethyl-7-[2-(2-t-butoxycarbonylprop-2-yloxyimino)-2-(fur-2-yl)acetamido]-ceph-3-em-4-carboxylate 1-oxide (syn isomer) (1.51 g) in N,N-dimethylformamide (3 ml) was stirred with benzotriazole (480 mg) for 4 days. The solution was diluted with dichloromethane and then dried, and purified by chromatography on Kieselgel, eluting with dichloromethane containing from 0 to 3% v/v acetone.

The diester so obtained (520 mg), together with anisole (0.5 ml), was treated with trifluoroacetic acid (2 ml) at 25° for 1 hour. The solution was then added dropwise with stirring to saturated aqueous sodium bicarbonate (50 ml) and ice (25 g). The mixture was stirred, whereafter ethyl acetate was added. The aqueous layer was separated and acidified under ethyl acetate to pH 2. The organic layer was separated, and the aqueous layer extracted with more ethyl acetate. The combined extracts were dried and concentrated to an oil, which was added dropwise to stirred petrol (b.p. 40°–60°). The white precipitate was filtered off, washed with petrol and dried to give the title dicarboxylic acid as a white powder (350 mg, 31%); $[\alpha]_D + 37°$ (c 1.02, DMSO); $\lambda_{max}$ (pH 6 phosphate buffer) 269 nm ($\epsilon$ 23,600); $\nu_{max}$ (Nujol) 1780 cm$^{-1}$ ($\beta$-lactam); $\tau$ (d$_6$-DMSO) values include 0.40 (d, J 8 Hz, N$\underline{H}$), 4.11 (dd, J 5 and 8 Hz, 7-$\underline{H}$) and 8.53 (s, C(C$\underline{H}_3$)$_2$).

EXAMPLE 22

The compound listed in Table 6 was prepared from the appropriate nucleophile using the method of Example 21.

TABLE 6

| Ex. No. | R² | P | Salt | $[\alpha]_D$ (DMSO) | $\lambda_{max}$, nm (pH 6 buffer) | $\epsilon$ | $\beta$-lactam $\nu_{max}$, cm$^{-1}$ (Nujol) |
|---|---|---|---|---|---|---|---|
| 22 | >C(CH₃)₂ | CH₂N (triazole) | — | +2° | 272 | 18,100 | 1780 |

| Ex. No. | $\tau$ values for d$_6$-DMSO at 100 MHz | | |
|---|---|---|---|
| | x | y | R$^q$ |
| 22 | 0.41 | 4.11 | 8.52 |

EXAMPLE 23

(a) Diphenylmethyl (6R,7R)-3-Azidomethyl-7-(2-tert-butoxycarbonylmethoxyiminophenylacetamido)-ceph-3-em-4-carboxylate syn-tert-Butoxycarbonylmethoxyiminophenylacetic acid (165 mg, 0.595 mmole) in methylene chloride (7 ml) was added slowly to a cooled solution of diphenylmethyl (6R 7R) 7-amino-3-azidomethylceph-3-em-4-carboxylate (250 mg, 0.595 mmole) and dicylohexylcarbodi-imide (150 mg, 0.7 mmole) in methylene chloride (7 ml). The reaction-mixture was stirred for 2.5 hr, then the precipitated dicyclohexylurea was filtered off. Removal of solvent from the filtrate left a residue which was dissolved in ethyl acetate. The solution was filtered and washed with 5% sodium hydrogen carbonate solution; 2N-hydrochloric acid, and water, then dried (Na$_2$SO$_4$) and evaporated, leaving the amide (288 mg, 87%) as a yellow foam.

(b) (6R,7R)-3-Azidomethyl-7-(2-carboxymethoxyiminophenylacetamido)-ceph-3-em-4-carboxylic acid Diphenylmethyl (6R,7R)-3-azidomethyl-7-(2-tert-butylcarbonylmethoxyiminophenylacetamido)-ceph-3-em-4-carboxylate (287 mg) was added to a mixture of anisole (0.3 ml) and trifluoroacetic acid (4 ml). The solution was stirred for 40 min. then evaporated. Benzene (50 ml) was added to the residue and removed by evaporation. The residue was partitioned between ethyl acetate and sodium bicarbonate solution; and the latter was acidified (10 N-HCl) under ethyl acetate, and extracted twice more with ethyl acetate. The organic extracts were washed with water and dried (Na$_2$SO$_4$), then evaporated, leaving an orange foam (183 mg). The foam was dissolved in ethyl acetate (2 ml) and added dropwise to vigorously stirred light petroleum (b.p. 40°–60°, 200 ml). Filtration gave the title-compound (100 mg, 51%), $\lambda_{max}$ (EtOH) 257.5 nm ($\epsilon$ 15,600), $\nu_{max}$ (Nujol) 2100(N$_3$), 1778($\beta$-lactam), 1724(CO$_2$H), 1670 and 1534 cm$^{-1}$(CONH), $\tau$(Me$_2$SO d$_6$) values include 0.17(d, J=8 Hz; CONH), 2.2–2.7(Ph), 4.10 (C-7H), 4.73(C-6H), 5.30(OCH$_2$), 5.58 and 6.04(AB quartet, J=13 Hz, CH$_2$N$_3$), 6.29 and 6.52(AB quartet, J=18 Hz, SCH$_2$).

EXAMPLES 24 AND 25

The following compounds were prepared as described for Example 23. Each compound is a syn isomer.

EXAMPLE 24

(6R,7R)-3-Acetoxymethyl-7-[2-(2-carboxyprop-2-yloxyimino)-2-phenylacetamido]-ceph-3-em-4-carboxylic acid Yellow solid, 87% yield, $\lambda_{max}$(EtOH) 257 nm ($\epsilon$ 15,500), $[\alpha]_D + 28.6°$ (c 1, DMSO), $\nu_{max-1}$(Nujol) 1781($\beta$-lactam), 1735 (acetate), 1722 and 1710 cm (2 carboxyl groups), $\tau$(Me$_2$SO d$_6$) 0.38(d, J=8 Hz) (CONH), 2.5(Ph), 4.04 (two doublets, J=8 and 5 Hz, C7-H), 4.75(d, J=5 Hz, C6-H), 4.98 and 5.29(AB quartet, J=13 Hz, CH$_2$OAc), 6.28 and 6.50(AB quartet, J=8 Hz, S-CH$_2$), 7.95 (COCH$_3$), 8.49(CMe$_2$).

EXAMPLE 25

(6R,7R)-3-Azidomethyl-7-[2-(2-carboxyprop-2-yloxyimino)-2-phenylacetamido]-ceph-3-em-4-carboxylic acid Off-white solid, 69% yield, $\lambda_{max}$(EtOH) 258 nm ($\epsilon$ 18,300), $[\alpha]_D + 12.5°$ (c 1, DMSO), $\nu_{max}$(Nujol) 1780($\beta$- lactam), 1720(CONH), 2090 cm$^{-1}$(N$_3$), $\tau_{96}$(Me$_2$SOd$_6$) 0.32 (CONH), 2.30–2.80(Ph), 4.02(C7-H), 4.78(C6-H) 5.57 and 6.08 (CH$_2$OAc), 6.24 and 6.52(S-CH$_2$), 8.48(CMe$_2$).

EXAMPLE 26

(6R,7R)-7-[2-(2-Carboxyprop-2-yloxyimino)-2-phenylacetaamido]-3-(1-pyridiniummethyl)-ceph-3-em-4-carboxylate (syn isomer)

Sodium iodide (13.05 g) was dissolved in water (3.6 ml) at 80°, and pyridine (3.3 ml) was added, then (6R,7R)-3-acetoxymethyl-7-[2-(2-carboxyprop-2-yloxyimino)-2-phenylacetamido]ceph-3-em-4-carboxylic acid (syn isomer) (3.03 g, 6 mmole). The mixture was stirred for 1 hr. at 80°, cooled and diluted with water (180 ml). The solution was washed with ether (75 ml) and ethyl acetate (75 ml), then acidified (pH 1) with 2N-hydrochloric acid. The solution was decanted from a brown sludge, washed again with ether and ethyl acetate, and brought to pH 6 (2 N-NaOH). The solution was concentrated under reduced pressure, diluted to 30 ml, and chromatographed on a column of XAD2 resin (300 g). Sodium iodide was eluted with water, then the column was run with 5% ethanol. Fractions having $\lambda_{max}$ca. 257 nm were combined and freeze-dried to give the pyridinium compound, 607 mg (19.3%), $\lambda_{max}$ (EtOH) 258 nm ($\epsilon$ 18,300), $\nu_{max}$(Nujol) 1770 ($\beta$-lactam), $\tau$(Me$_2$SO d$_6$) 0.59, 1.49 and 1.89 (pyridinium), 2.30–2.80(Ph), 4.22(C-7H), 4.88(d, J=5 Hz; C-6H), 4.20 and 4.80 (CH$_2$N$^+$), 8.50 and 8.59 (CMe$_2$).

EXAMPLE A

This example illustrates the formulation of a pharmaceutical composition.

Dry Powder for Injection

Sterile (6R,7R)-7-[2-carboxyprop-2-yloxyimino-2-(fur-2-yl)acetamido]-3-pyridiniummethyl-ceph-3-em-4-carboxylic acid, sodium salt (syn-isomer) is filled into glass vials, the claimed contents of each container being 500 mg. or 1.00 g. of the antibiotic as desired. Filling is carried out asceptically under a blanket of nitrogen. The vials are closed using rubber discs or plugs held in position by aluminium sealing rings, thereby preventing gaseous exchange or in gress of micro-organisms. The product would be intended for reconstitution with water for injections or other suitable sterile vehicle shortly before administration.

We claim:

1. A compound selected from the group consisting of a cephalosporin antibiotic of the formula:

R.C.CO.NH─┐ H H S
   ‖        ├──┤   \
   N        │   ├──N   ═CH$_2$Y
    \    R$^a$  O      │
     \    │           COOH
      O.C.COOH
         │
         R$^b$ wherein
R is thienyl or furyl;
R$^a$ is hydrogen, methyl, ethyl, propyl, isopropyl, butyl, allyl, cyclohexyl or phenyl;
R$^b$ is hydrogen, carboxy, C$_2$–C$_5$ alkoxycarbonyl, methyl, ethyl, propyl, isopropyl, butyl, allyl, cyclohexyl or phenyl;

or R$^a$ and R$^b$ together with the carbon atom to which they are attached form a C$_{3-7}$ cycloalkylidene group;
Y is the residue of a nitrogen nucleophile which is a tri(C$_{1-6}$ alkyl) amine, or a heterocyclic tertiary amine which is a pyridine, pyrimidine, pyridazine, pyrazine, pyrazole, imidazole, triazole, thiazole, benzotriazole or purine, which may be substituted by a C$_{1-6}$ alkyl, phenyl, naphthyl, phenyl C$_{1-6}$ alkyl, (C$_{1-6}$ alkoxy) methyl, (C$_{2-7}$ alkanoyloxy)methyl, formyl, C$_{2-7}$ alkanoyl, C$_{2-7}$ alkanoyloxy, carboxy, C$_{2-7}$ alkoxycarbonyl, carboxy (C$_{1-6}$ alkyl), sulpho, C$_{1-6}$ alkoxy, phenoxy, phenyl C$_{1-6}$ alkoxy, C$_{1-6}$ alkylthio, phenylthio, phenyl C$_{1-6}$ alkylthio, cyano, hydroxy, carbamoyl, N-(C$_{1-6}$ alkyl) carbamoyl, N,N-di(C$_{1-6}$ alkyl) carbamoyl, N-(hydroxy C$_{1-6}$ alkyl)carbamoyl or carbamoyl C$_{1-6}$ alkyl group; or azido, and a physiologically acceptable salt, ester or a 1-oxide thereof.

2. The compound of claim 1 which is (6R,7R)-3-azidomethyl-7-[2-carboxymethyloxyimino-2-(fur-2-yl) acetamido]ceph-3-em-4-carboxylic acid (syn isomer).

3. The compound of claim 1 which is (6R,7R)-7-[2-carboxymethoxyimino-2-(fur-2-yl)acetamido]-3-pyridiniummethyl-ceph-3-em-4-carboxylate (syn isomer).

4. The compound of claim 1 which is (6R,7R)-7-[2-carboxyprop-2-yloxyimino-2-(fur-2-yl)-acetamido]-3-pyridiniummethyl-ceph-3-em-4-carboxylic acid (syn isomer).

5. The compound of claim 1 which is sodium (6R,7R)-7-[2-(carboxyprop-2-yloxyimino)-2-(fur-2-yl)-acetamido]-3-pyridiniummethylceph-3-em-4-carboxylate (syn isomer).

6. The compound of claim 1 which is (6R,7R)-3-[(4-carbamoylpyridinium)methyl]-7-[2-carboxyprop-2-yloxyimino-2-(fur-2-yl)acetamido]ceph-3-em-4-carboxylate (syn isomer).

7. The compound of claim 1 which is (6R,7R)-3-[(3-carboxymethylpyridinium)methyl]-7-[2-carboxyprop-2-yloxyimino-2-(fur-2-yl)acetamido]ceph-3-em-4-carboxylate (syn isomer).

8. The compound of claim 1 which is (6R,7R)-7-[2-cyclopent-1-yloxyimino-2-(fur-2-yl)acetamido]-3-pyridiniummethylceph-3-em-4-carboxylate (syn isomer).

9. The compound of claim 1 which is (6R,7R)-7-[2-cyclobut-1-yloxyimino-2-(fur-2-yl)acetamido]-3-pyridiniummethylceph-3-em-4-carboxylate (syn isomer).

10. The compound of claim 1 which is (6R,7R)-7-[2-carboxyprop-2-yloxyimino)-2-(fur-2-yl)acetamido]-3-pyridaziniummethylceph-3-em-4-carboxylic acid (syn isomer).

11. The compound of claim 1 which is (6R,7R)-7-[2-carboxyprop-2-yloxyimino-2-(fur-2-yl)acetamido]-3-(thiazol-3-ylmethyl)ceph-3-em-4-carboxylic acid (syn isomer).

12. The compound of claim 1 which is (6R,7R)-3-[(3-carbamoylpyridinium)methyl]-7-[2-carboxyprop-2-yloxyimino-2-(fur-2-yl)acetamido]ceph-3-em-4-carboxylate (syn isomer).

13. The compound of claim 1 which is (6R,7R)-3-[(3-sulphopyridinium)methyl]-7-[2-carboxyprop-2-yloxyimino-2-(fur-2-yl)acetamido]ceph-3-em-4-carboxylate (syn isomer).

14. The compound of claim 1 which is (6R,7R)-3-(benzotriazol-1-ylmethyl)-7-[2-(2-carboxyprop-2-yloxyimino)-2-(fur-2-yl)acetamido]ceph-3-em-4-carboxylic acid (syn isomer).

15. A compound selected from the group consisting of a cephalosporin antibiotic of the formula

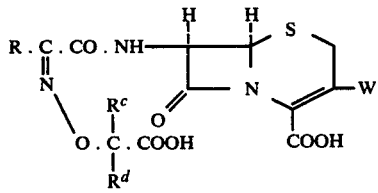

wherein R is thienyl or furyl, $R^c$ is methyl, ethyl, propyl, allyl or phenyl and $R^d$ is hydrogen, carboxy, methyl, ethyl, propyl, allyl or phenyl or $R^c$ and $R^d$ together with the carbon atom to which they are attached form a cyclobutylidene, cyclopentylidene or cyclohexylidene group and W is selected from (i) the group $-CH_2G$ where G is the residue of a nitrogen nucleophile selected from compounds of the formula

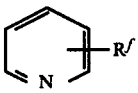

wherein $R^f$ is hydrogen, carbamoyl, carboxymethyl or sulpho, and pyridazine; and (ii) azidomethyl; and a physiologically acceptable salt or 1-oxide thereof.

* * * * *